(12) United States Patent
Schmittmann et al.

(10) Patent No.: US 12,153,025 B2
(45) Date of Patent: Nov. 26, 2024

(54) METHOD FOR CALIBRATION, AND MEASUREMENT AND ANALYSIS METHOD

(71) Applicant: Dräger Safety AG & Co. KGaA, Lübeck (DE)

(72) Inventors: Matthias Schmittmann, Hamburg (DE); Johannes Weber, Hamburg (DE); Paul Weber, Berlin (DE); Arne Jünemann, Hamburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 647 days.

(21) Appl. No.: 16/482,937

(22) PCT Filed: Oct. 13, 2017

(86) PCT No.: PCT/EP2017/076244
§ 371 (c)(1),
(2) Date: Aug. 1, 2019

(87) PCT Pub. No.: WO2018/141427
PCT Pub. Date: Aug. 9, 2018

(65) Prior Publication Data
US 2019/0353624 A1 Nov. 21, 2019

(30) Foreign Application Priority Data
Feb. 2, 2017 (DE) .................. 10 2017 201 680.9

(51) Int. Cl.
*G01N 30/02* (2006.01)
*G01N 33/00* (2006.01)

(52) U.S. Cl.
CPC ......... *G01N 30/02* (2013.01); *G01N 33/0006* (2013.01); *G01N 33/0021* (2013.01); *G01N 33/0062* (2013.01); *G01N 2030/025* (2013.01)

(58) Field of Classification Search
CPC ............... G01N 30/02; G01N 33/0006; G01N 33/0021; G01N 33/0062; G01N 2030/025
See application file for complete search history.

(56) References Cited

U.S. PATENT DOCUMENTS

| 4,670,405 A | 6/1987 | Stetter |
| 4,818,875 A * | 4/1989 | Weiner .................... G01J 3/108 |
| | | 250/493.1 |

(Continued)

FOREIGN PATENT DOCUMENTS

| CN | 102062722 A * | 5/2011 |
| CN | 103513029 A | 1/2014 |

(Continued)

OTHER PUBLICATIONS

International Search Report and Written Opinion mailed Jan. 5, 2018, directed to International Application No. PCT/EP2017/076244; 21 pages.

(Continued)

*Primary Examiner* — Jamel E Williams
*Assistant Examiner* — Alex T Devito
(74) *Attorney, Agent, or Firm* — McGlew and Tuttle, P.C.

(57) ABSTRACT

A method for a multistep analysis of a measuring program of a portable gas measuring device includes performing a factory setting of the portable gas measuring device, connecting a container having a known gas standard and performing a reference measurement, wherein a multidimensional reference measurement is recorded, selecting a measuring program for target materials from a list on the device, performing a measurement on a sample in dependence on the selected measuring program, wherein a multidimensional measured variable is recorded, automatically performing an analysis to identify at least one of the one or more target materials in the sample and the respective concentrations thereof, wherein the analysis is based on the (Continued)

multidimensional measured variable from the measurement on the sample, the multidimensional reference measurement for the gas standard, the values for the plurality of target materials or measuring programs, and the factory setting for the portable gas measuring device.

23 Claims, 4 Drawing Sheets

(56) References Cited

U.S. PATENT DOCUMENTS

| | | | |
|---|---|---|---|
| 5,313,061 | A | 5/1994 | Drew |
| 6,627,444 | B1 * | 9/2003 | Goledzinowski .... G01N 27/622 250/281 |
| 6,672,129 | B1 * | 1/2004 | Frederickson ...... A61M 15/025 73/1.06 |
| 2002/0092339 | A1 * | 7/2002 | Lee .................. G01N 33/0011 73/23.2 |
| 2008/0036742 | A1 | 2/2008 | Garmon |
| 2008/0121016 | A1 | 5/2008 | Shah |
| 2012/0192623 | A1 | 8/2012 | Adami |
| 2014/0156202 | A1 | 6/2014 | Floridia et al. |
| 2016/0077071 | A1 | 3/2016 | Chancey |
| 2020/0158655 | A1 | 5/2020 | Ringemann et al. |

FOREIGN PATENT DOCUMENTS

| | | | | |
|---|---|---|---|---|
| CN | 103563043 | A | | 2/2014 |
| CN | 103644933 | A | | 3/2014 |
| CN | 104854457 | A | | 8/2015 |
| DE | 3507386 | | | 9/1985 |
| DE | 102016006972 | A1 * | 12/2016 | ......... G01N 27/4065 |
| DE | 102015219838 | | | 4/2017 |
| EP | 2065704 | | | 6/2009 |
| EP | 2570807 | A1 * | 3/2013 | ......... G01N 27/4163 |
| HU | 195336 | | * | 4/1988 |
| KR | 1998041797 | | * | 9/1998 |
| KR | 100664313 | B1 * | 1/2007 | |
| KR | 20110046179 | | * | 5/2011 |
| WO | WO-03003162 | A2 * | 1/2003 | ............. G06F 19/28 |

OTHER PUBLICATIONS

Action dated Feb. 19, 2018, directed to DE Application No. 1020172016809; 4 pages.

Search Report dated May 26, 2021, directed to CN Application No. 201780089007.7; 3 pages.

Zhu, Hongsheng. (Oct. 2009). "Several Issues Should Be Considered When Using Virtual Instrument To Build Automatic Test System," Chinese Journal of Scientific Instrument 30(10): 88-91.

* cited by examiner

METHOD FOR CALIBRATION, AND MEASUREMENT AND ANALYSIS METHOD

CROSS-REFERENCE TO RELATED APPLICATIONS

This application is a U.S. national stage patent application of International Patent Application No. PCT/EP2017/076244, filed Oct. 13, 2017, which claims the priority of DE 10 2017 201 680.9, filed on Feb. 2, 2017, the entire contents of each of which are incorporated herein by reference.

FIELD OF THE INVENTION

This invention generally relates to gas measuring devices used in industry, operational safety, environmental protection, and science to determine the presence and concentration of chemical compounds in the air or in enclosed volumes.

BACKGROUND OF THE INVENTION

Gas measuring devices are used in industry, operational safety, environmental protection, and science to determine the presence and concentration of chemical compounds in the air or in enclosed volumes, often with the goal of detecting traces of materials harmful to the environment and health. For this purpose, samples can either be taken for later laboratory studies or measurements can be carried out directly on location using gas measuring devices. Laboratories typically offer a higher level of sensitivity, selectivity, and precision of the measurement, since the stationary gas measuring devices are higher-performance and the conditions and sequences in the protected laboratory environment can be better controlled by trained personnel. Due to the increasing availability of more complex measuring devices, which are compact and transportable at the same time, new demands result for the sequence of the overall measuring method to also enable precise and repeatable measurements in the field test, without taking away the advantages of a rapidly usable device from the user due to cumbersome preparation.

In the context of the present patent application, gas measuring devices are understood as those measuring devices which determine the chemical composition and concentration of gases, not those which primarily measure other properties (for example, temperature) of gases. Various gas measuring devices differ in the construction and in the various detection methods, less in the method of application. A full method cycle in the case of the user firstly comprises a preparation (calibration and often flushing) of the gas measuring device, then the measurement of a sample and subsequent analysis. The sample is either introduced directly in gaseous form into the gas measuring device or vaporized in a furnace and/or an enrichment unit. During the measurement, a signal is recorded, which is compared to the signal levels of prior measurements, in the simplest case a standardization measurement, which is carried out once before delivery by the producer or regularly by the user. Alternatively or additionally, the measurement signal is also compared or offset using expected values of the signal level from theoretical models. The analysis always requires the comparison of the sample measurement to an experimentally determined or theoretical reference. Above all in the field test, different conditions exist from measurement to measurement, which can be differentiated into external factors (temperature, air pressure, ambient humidity) and internal factors (power variations, soiling, aging and wear of components of the gas measuring device). To execute a reliable analysis, the deviation of the variable conditions has to be corrected during the measurements. To compare the measurement signal at the detector and a theoretical model, they have to be linked via a mathematical function, the so-called device function, in which the information about the gas measuring device is contained.

Measuring methods which dispense with an absolute measurement result and instead perform the analysis based on the relative measurement are more elegant. Such a relative method is the linkage of the measurement on an unknown sample to a measurement on a known reference. Such a reference calibration is typically executed before the sample measurement. A gas mixture having known chemical composition and concentration is suitable as a reference. It can either be kept ready directly in gaseous form in a container, wherein the mixture can be more concentrated and compressed in the container and can first be diluted in a carrier gas for the calibration. Alternatively, the reference materials can be kept ready in the liquid state, wherein these liquid reference materials for the calibration are vaporized in a furnace or diffuse permanently through the membrane of a permeation tube. In addition to a calibration measurement using the main detector, the measurements of auxiliary sensors, for example, thermometers, or data generated or stored in the gas measuring device can also be incorporated into the correction.

It is also advisable or even prescribed in the case of simple gas measuring devices, which carry out a direct measurement using a single detector without separation of the materials, to perform a calibration at least on every day on which the device is used. New calibrations are generally necessary if the external conditions change, such as temperature, humidity, and air pressure, since they can have effects on the materials, the measuring procedure, and thus the result. A calibration on a known reference sample permits a systematic deviation to be established and corrected. A repeated measurement on a known, unchanging reference sample enables conclusions about the stability of the measuring method and systematic changes due to aging of the device. In simple detectors having one-dimensional measurement variable, the calibration often corresponds to a standardization of the measurement around a factor to be determined during the calibration. Additional challenges result for more complex measuring methods, in which a multidimensional measurement, such as a gas chromatogram, is recorded and analyzed, since a proper calibration in these cases requires a correction via a corresponding function, i.e., for example, the coefficients of a polynomial correction function have to be determined. Carrying out such a computation is not possible for every user and delays the application in the field, whereby an important advantage in relation to laboratory methods, namely the availability at short notice of measurement results, is reduced.

Portable simple gas measuring devices having direct display of the measurement results (so-called scale display or direct-reading measurement), either for continuous or punctiform measurement, which are available with a large selection of detectors and configurations, which are suitable for the respective target materials and specifications, are a first prior art. These devices share the feature that they can record a one-dimensional signal or a time series of one-dimensional signals in each case for a specific material or a group of materials ("dimension" is understood in the present case as the number of different materials/material groups, i.e., "one-dimensional" only relates to a single material or material group). In older devices, an unprocessed detector signal is displayed as the measured value, which the user then has to convert themselves to determine the concentration of the target material. In many current instances, this conversion is already carried out by an integrated processing unit of the gas measuring device and the detector signal is associated with a concentration of the detected material. The data from the calibration measurement are also automatically processed in these devices and are already offset in the measured value shown. This ability to read the information relevant to the user directly in conjunction with a simple operation of these devices enables a reliable usage by the user without scientific education. The selection and performance of the method steps of flushing, calibration, and measurement does not require complex inputs. For this reason as well, these gas measuring devices having one-dimensional measured variable are also widespread as portable measuring devices for field tests. As a significant disadvantage of these devices, an analysis, the result of which determines the respective concentrations of multiple materials separately or at least identifies individual materials, cannot be performed using a one-dimensional measured variable. In the case of a plurality of materials to which the detector is sensitive, only the summation signal can be determined. Moreover, many false-positive measurements occur, in which a high signal is measured, which arises due to irrelevant materials (for example, water vapor). Such measuring devices having direct display are often only used as an aid to subsequently take samples which are analyzed in a laboratory.

Laboratory devices for the measurement of gases which are conceived for use by scientists or other trained technicians are a second prior art. Widespread laboratory devices are gas chromatographs, mass spectrometers, optical spectrometers, or combinations of these device classes. In such devices, a multidimensional measurement result is recorded for each measurement point: In gas chromatographs (GC), a chromatogram is recorded, in which the intensity at a detector is plotted against the retention time in a chromatography column. In mass spectrometers (MS), a mass spectrogram is recorded, in which the frequency of materials is plotted as a function of the mass-charge ratio thereof. In optical spectrometers, the transmission, absorption, or reflection of light is measured at various wavelengths in and/or on the gases. In the higher-dimensional methods, for example, the GC-MS, multidimensional measurement results are accordingly obtained. With continuous or regularly juxtaposed measurement points, the measurement can additionally be noted as a time series, which is not to be understood as an additional dimension of the measurement, however, since each measurement point in the time series is analyzed individually. The multidimensional measurement enables a separation of individual components of the signals, which are associated with various materials. It is to be noted here that, for example, in optical spectroscopy, the materials are not physically separated, but rather can only be identified via the characteristic measured values. The analysis of these signals is usually carried out presently in an assisted or even automated manner in a computer program. The advantage of laboratory devices is the high performance capacity thereof, which results due to a device conceived without compromise. In contrast, the disadvantage of laboratory devices is the high time expenditure and work expenditure by a technician. These devices are unsuitable for use in the field test, at best they are installed in a measuring vehicle.

Miniaturized laboratory devices for mobile use, which permit a material-specific concentration measurement and record a multidimensional measured variable for each measurement point for this purpose, are a third prior art. There are also devices having different detectors in this class (for example, GC, MS, spectrometer). A connection of the simple application of the first prior art for mobile gas measuring devices with the high precision and reliability of the second prior art for laboratory gas measuring devices is not achieved in this case. Early experiments for implementing material-separating laboratory methods in portable gas measuring devices often resulted in unmanageably heavy devices, which additionally required a laptop computer for control. However, even if the technology were successfully miniaturized, many producers often take over the method unchanged from laboratory devices having corresponding demands on the time and knowledge of the user. This is unsatisfactory, so that such devices have not been able to find widespread success.

Modern miniaturized gas measuring devices, which have been developed with the options of so-called digitization, are proposed by the applicant (DE 10 2015 219 838). Commercially-available and cost-effective processing units and digital data connections are used, as are available in mass production in digital mobile devices, to thus make use of effectively unlimited data memories and high-performance processing units in gas measuring technology, which are provided in the virtual part of the method either by the processing unit of the gas measuring device, a connected mobile computer, or even by a spatially separate server, which is connected via a network connection to the gas measuring device. This performance capacity enables the rapid execution of complex measuring programs and analysis algorithms and also more accessible operation and display of the gas measuring device.

In spite of this modernity, these gas measuring devices also require a calibration by the user. This takes place in such a manner that a calibration in the form of a measurement on a gas standard of known chemical composition and concentration is performed regularly by the user using the gas measuring device. Experience has shown that many users learn a method once and repeat it. The learning curve for advanced operation of the gas measuring devices is comparatively flat, above all because the users frequently have a very high level of knowledge and experience in the use of gas measuring technology. In this case, even experienced users value simplified operation and time savings thanks to rapid measurement. An adaptation of the parameters to changed conditions is often omitted. The situation thus exists that for a simple, one-dimensional measurement, the calibration is easily successful and is also performed by the user. However, the calibration is excessively complicated in the case of complex, multidimensional measurements.

SUMMARY OF THE INVENTION

According to some embodiments, an objective is to also make the advantages of simple calibration usable for the multidimensional measurement of a correspondingly complex gas measuring device. According to some embodiments, persons from operational safety or the factory fire department are enabled to use measuring devices having higher performance, which were heretofore exclusively reserved for highly-qualified persons from laboratory analytics.

In a method for the multistep calibration of measuring and analysis methods for portable gas measuring devices having connected control unit and connected analysis unit having a detector unit for gas chromatography, for selective detection of a plurality of chemical compounds, wherein in a first step after production, a factory setting of the gas measuring device is performed, wherein a database is generated for a plurality of target materials and/or measuring programs for the respective gas measuring device, in a second step, a container having a known gas standard is connected to the gas measuring device by the user and a reference measurement is carried out on this gas standard, in which a multidimensional measured variable, in particular a gas chromatogram, is recorded, in a third step, a measuring program for one or more target materials is selected from a list by the user, which were installed on the gas measuring device by the producer or can be created by the user, in a fourth step, the measurement is triggered, wherein the control unit executes the measuring method in dependence on the selected measuring program, in which a multidimensional measured variable is recorded, and in a fifth step, the analysis unit automatically carries out an analysis to identify the target materials present in the sample and the respective concentrations thereof, wherein an algorithm processes multiple input variables, among them the multidimensional measured variable from the measurement on the sample, the multidimensional reference measurement on the gas standard, the values for the target material or the target materials for the respective program, and the factory setting for the gas measuring device.

Firstly, several terms used will be explained: a production is understood as the actual initial production (production), but also a restoration in the meaning of a repair.

Selective detection is understood to mean that the analysis of the multidimensional measured variable enables a differentiation between the signal components of various target materials and possible interfering signals in the measurement and thus permits the computation of presence and concentration for one or more target materials, the presence of which in the sample does not have to be known. For example, for an unknown sample gas, a concentration KX is determined for material X and concentration KY is determined for material Y, wherein further components of the signal are identified as background or interference signals. In contrast, in the case of nonselective detection, it is not possible to differentiate between various materials measurable by the detector unit, for example, a hazardous target material, a harmless further material, and/or interference signals, because of which non-unambiguous or false positive measurement results can occur. A fundamentally selective detection can also only reliably function from a certain signal level, because of which the sufficient sensitivity of the detector unit for all materials present in the sample and/or the concentration thereof is required for the selectivity. Those cases in which all components of the signal are clearly separated, for example, as nonoverlapping signal peaks, which are overlaid with a constant background signal and low noise, are simple to solve for an automated analysis. A challenge for an analysis algorithm are those cases in which the signal characteristics of multiple target materials are very similar for a specific detector unit or the measurement signals of multiple target materials are not independent, i.e., a so-called cross sensitivity exists, whereby in spite of adequate sensitivity for the individual materials, selectivity of the detector unit is not provided for this measurement.

A detached database is understood as a database which is arranged spatially remote in another device unit.

A program is understood in the present case as a controlled sequence of a measurement ("measuring program").

Health-harmful materials are understood as those chemical compounds which have a direct toxic effect for humans or have a negative effect on the health due to long-term consequences, in particular increase the risk for cancers. Depending on the field of law and area of application, different legal rules or other rules apply to establish the limiting concentration of hazardous materials. In the field of operational safety in Germany, the hazardous materials are defined in the technical rules TRGS 900 and TRGS 910 with the respective workplace limiting values, acceptance concentrations, and/or tolerance concentrations, and these are possibly supplemented by operational rules. Specific examples of hazardous materials with respect to the invention are in particular benzene, 1,3-butadiene, trichloroethene, ethylene oxide, and toluene (the latter from a concentration of 50 ppm). The materials isobutene and toluene (each in a concentration of 10 ppm), which are harmless according to the technical rules, are suitable as reference materials for a calibration measurement for this group. It is clear from the example of toluene that depending on the concentration, the materials can be significant for the method as health-harmful target materials or harmless calibration materials.

The core of the invention is to provide a multistep calibration method, which links a setting (and/or calibration) at the factory with a calibration by the user, in conjunction with an assisting automation, which adapts and possibly corrects measuring and analysis procedures executed by the user in use. Both parts require one another for this purpose.

In a first part of the method, in this case the gas measuring device is comprehensively set by the producer and prepared measuring programs are installed and test measurements are carried out. These data are part of the database, which the algorithm can access for analysis. This first part is carried out after the production and after maintenance and repairs, before the gas measuring device is supplied. The second part of the method is first executed by the user as a routine. During the calibration by the user, one (or more) reference measurements are performed on a known gas standard, which does not have to contain target material. Before the measurement, the user selects a measuring program, which is optimized for one or a group of target materials. The gas measuring device possibly offers additional options to the user, which are available for the respective program. The measurement is now performed, wherein the parameters of the measurement are adapted using items of information from the stored database. During the analysis, the items of information from sample measurement, calibration, and the factory-installed database of programs, materials, and calibration are processed without further inputs of the user. The measured concentrations of the identified materials in the sample are immediately displayed.

The method according to some embodiments of the invention enables a combination of the low level of effort of a program selection and simple calibration on a gas standard, as is typical per se for simple handheld measuring devices, with a complex computer-assisted measuring and analysis program, as has heretofore only been possible for scientific personnel having laboratory devices in a laboratory environment. Such a novel method becomes possible due to the continued refinement of miniaturizations of material-specific transportable gas measuring devices, which have moved so far away technologically from the laboratory devices that they require separate methods. Such a method becomes practicable due to the availability of higher processing power and larger data memories in digital mobile devices, which enable an automated execution of more demanding processing and data operations for calibration, measuring programs, and analysis and offer an accessible user interface to the user. In this method, the second method part of the calibration performed by the user is equivalent to the method typical in the widespread simple measuring devices, because of which the execution of these method steps is known to those users who have heretofore used a nonspecific device. A better adaptation of the measuring and analysis method to external factors permits the reliable application in changing environmental conditions, while the adaptation to changed internal factors extends the periods of time before parts have to be replaced. The recording of all calibration measurements as a series permits conclusions about the state of the gas measuring device and the necessity of a replacement of parts of the gas measuring device.

A factory calibration is advantageously carried out by the producer, in which intrinsic device correction values are determined for the respective gas measuring device and stored in a database. A better consideration of device-individual special characteristics can be achieved using the factory calibration, whereby the measuring accuracies are increased.

The gas measuring device is advantageously a gas chromatograph, which is embodied as a miniaturized, portable measuring device for field tests at less than 1.5 kg total weight.

Furthermore, the gas measuring device is advantageously embodied as a miniaturized, portable measuring device for field tests. Thanks to the miniaturization, a high level of portability is ensured, whereby the usage spectrum is expanded.

In the calibration measurement, a gas mixture of the materials isobutene (A) and toluene (B), each in harmless concentration, in particular respective concentrations between 1 ppm and 100 ppm in air or nitrogen, is preferably used as the gas standard, wherein the target materials of the measuring program of the sample measurement are the materials benzene (X) and 1,3-butadiene (Y), which are already harmful at low concentration, and the detection limit of which is less than 1 ppm, advantageously even less than 1 ppb in each case. Therefore, signal components of further unknown materials (Z) in the measurement signal can also be differentiated from the signal components of the target materials (X, Y) in the analysis.

The portable gas measuring device is advantageously equipped with or connected to a mobile processing unit, which can access databases of external processing units via a wireless connection. The actual gas measuring device can thus be embodied as even smaller and thus more portable. Furthermore, the access to external databases/processing units has the advantage that more extensive analysis functions can be executed on the processing unit, and also possibly with recourse to external databases. A type of expert system can thus be used, whereby the quality of the measurement may be further increased. The latter applies above all if the gas measuring device retrieves additional data from external databases, which are processed by the algorithm of the analysis.

Preferably, the gas measuring device stores the multidimensional measured variable of successive measurements in a database and performs a function test of the gas measuring device in this case via an algorithm from the measurement results of the reference sample, after which the gas measuring device displays items of information about the state of the gas measuring device, in particular a warning about required maintenance, to the user. The operational reliability and the robustness of the measurements can thus be increased. Furthermore, possible creeping worsening, for example, of the detector unit, can also be recognized early and a repair can be prompted before worsening of the measurement quality occurs. The analysis and measuring quality is thus further enhanced.

In a corresponding application, to improve the running measuring mode, it can be provided that the gas measuring device incorporates prior measurement results, which were also generated using the selected program, from an internal database in the algorithm of the analysis. Alternatively or additionally, the gas measuring device can incorporate measurement results which were also generated using the selected program by other gas measuring devices from an internal or external database in the algorithm of the analysis. In this manner, by matching with earlier intrinsic measurements and/or the measurements of other measuring devices, which are stored in particular in the external database, an improvement of the analysis algorithm of the analysis can be achieved. In particular, filters can thus be better parameterized in the signal processing and possible model errors can be reduced. Overall, a significant enhancement of the result quality can thus be achieved.

The measuring method according to some embodiments is advantageously adapted automatically to the measurement results of auxiliary detectors, in particular the external temperature. It may thus be checked whether the measurements can be continued with unchanged quality or whether a renewed calibration by the user is required for preservation.

According to a particularly advantageous aspect of the invention, the gas measuring device automatically proposes changes to the measuring program to the user, which it has computed from the prior measurements stored in the databases in an algorithm as parameters which are probably more suitable. In this manner, an enhancement of the analysis quality can be achieved utilizing prior knowledge. Alternatively or additionally, it can be provided that the algorithm of the analysis, after a prior pass of the analysis is evaluated as failed according to specific criteria, automatically subsequently adds further target materials from a database into the program of the analysis, which supplement the measuring program preselected by the user, wherein this procedure is repeated until either the analysis becomes successful or a specific number of repetitions and/or a time span is exceeded. An iterative method control is thus achieved, which can achieve a higher analysis quality in the case of convergent behavior and reacts appropriately in the case of divergent behavior, for example, by repetition or termination. Unnecessary delays are thus avoided and nonetheless a significant enhancement of the analysis quality is achieved.

Furthermore, it can be provided that the measurement is carried out in parallel by multiple users, and during the measurement use, the setting of the measuring programs and/or data are transferred between multiple gas measuring devices connected in networks and/or to a central server.

In one advantageous embodiment, the calibration is carried out using a gas standard, which is kept ready at the gas measuring device or in the gas measuring device, possibly also in parallel during the sample measurement. The manual connection of a gas standard or even the entire method step of calibration by the user is saved by this further step, since the calibration is carried out during a (or during every) normal measurement. The possibility is advantageously to exist of optionally only carrying out the calibration without sample or not also mixing the gas standard into the sample, to be able to avoid possible problems with cross sensitivities and overlapping signals of calibration and sample in a measurement. The gas standard can be kept ready in liquid form in permeation tubes or in gaseous form compressed in cartridges inside or on the gas measuring device. If the gas standard used is injected in parallel to the sample measurement into the detector unit (=internal standard), none of the target materials can be contained therein and it has to have a sufficiently differing characteristic from the expected characteristic of the target materials to be able to be separated cleanly from the signal of the sample. If the calibration is carried out by the user between measurements, in contrast, it is advantageous to select similar or identical materials as the gas standard.

An automatic recognition and avoidance of cross sensitivities can be expediently provided. For this purpose, in a measuring program for measuring multiple target materials (or a selection of a group of target materials from a list of materials), the cross sensitivities are determined and/or retrieved, and in the case of relevant cross sensitivities, the control program of the measurement and/or the algorithm of the analysis at the analysis unit is automatically adapted so that a known cross sensitivity for the target materials is avoided. The user is thus relieved of this difficult and possibly very error-prone task, which counteracts the risk of unrecognized (possibly severe) incorrect measurements.

The portable gas measuring device is preferably used as a part or attachment on a vehicle and/or aircraft which is remote-controlled by the user and/or self-controlled, in particular a robot drone, as a carrier unit, wherein preferably the gas measuring device is connected via a wireless connection to an external processing unit.

BRIEF DESCRIPTION OF THE DRAWINGS

The invention is explained hereafter with reference to the appended drawing, in which advantageous exemplary embodiments are shown. In the figures.

DETAILED DESCRIPTION OF THE INVENTION

Figure 1:
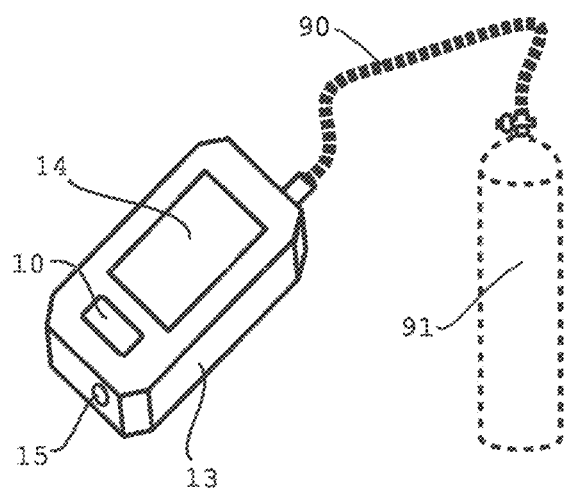
FIG. 1 shows an overview illustration of a gas measuring device according to a first exemplary embodiment of the invention connected to a test gas (gas standard)

A portable gas measuring device 1 as a portable gas analysis device having a gas bottle 91 connected thereto via a connecting hose 90 is illustrated in FIG. 1. The portable gas measuring device 1 comprises a housing 13, on the end face of which an inlet 15 for a gas supply is arranged. A display unit 14 and an operating element 10 are arranged on an upper side of the housing 13. Furthermore, a measuring unit, a processing unit, and an electrical energy accumulator (not shown) are arranged in the interior of the housing 13. It is to be noted that the processing unit and/or display unit 14 can optionally also be arranged externally, i.e., outside the housing 13. It is then a detached processing unit or display unit, respectively. Typical transmission means are provided for the connection, in particular short-range radio (via Bluetooth or WLAN). A gas mixture having defined composition (gas standard 9) is contained in the gas bottle 91. It contains a carrier gas and a further component and preferably still further components (one-dimensional or multidimensional gas standard, respectively). In principle, the method according to the invention provides a calibration before beginning the measuring mode. The portable gas analysis device 1 is thus set to the respective measuring requirements and measuring environment. A first part thereof generally only has to be carried out once, namely following production 11 of the portable gas analysis device 1, wherein various, generally material-specific programs and tables 4 are also installed on the portable gas analysis device 1. In general, this will take place while still in or under responsibility of the producing factory. In this case, this can be a factory setting 21 in the scope of the quality check of the producer or a more complex factory calibration 21'. In general, this only has to be carried out once per portable gas analysis device 1. An exception thereof is a repair 19, in particular an extensive repair, which is considered to be a restoration; in this case, the factory setting or factory calibration is carried out again. A second part of the calibration is performed by the user themselves, specifically in dependence on the provided measuring program. The performance by the user takes place on location, which means that both chronologically and also spatially, the closest possible linkage between user calibration 31 of the portable gas analysis device 1 and its use for measuring 41 is to be achieved. In this manner, errors because of changing, deviating environmental conditions can be minimized or practically precluded.

This will be explained in greater detail hereafter on the basis of two exemplary embodiments, wherein the first example stands for a simpler variant and the second example stands for a more complex variant.

Exemplary Embodiment 1

In a first exemplary embodiment, a gas chromatograph is embodied as an integrated portable gas measuring device. Each portable gas measuring device is calibrated 21' by the producer after the production 11 and a selection of programs 40 for various materials is installed 12. The user performs a calibration 31 using a gas standard 9 supplied by the producer in the respective environmental conditions at the beginning of each measuring day, wherein the gas measuring device records a gas chromatogram having multiple specific signal peaks and stores it as calibration data 32. The user can now use the portable gas measuring device for an array of measurements in the field, as long as the calibration is valid, i.e., in particular the environmental conditions do not change excessively strongly or a prescribed period of time is not exceeded. During the measurement, the portable gas measuring device executes the measuring method 41 using the parameters which were stored in the selected program 40, wherein the measured data 42 thus measured are corrected using values from the factory calibration 21. During the analysis, the measurement curve is calibrated 32 using the reference values of the calibration on the gas standard in both coordinates (typically the intensity linearly and the retention time using a polynomial function). An analysis algorithm 50 implemented in the processing unit simulates a model for the expected signal peaks of the target materials, which are specified in the program 40, and adapts the parameters for material concentrations of the model iteratively until model and calibrated measurement curve correspond or the method is terminated unsuccessfully. A so-called device function implemented in the algorithm links model and measured values in this case. As a result, the portable gas measuring device directly displays 51 the determined concentrations of the identified compounds in the sample and optionally stores them in a measurement database 52.

After the completed single measurement, the user can continue with further measurements, if the calibration is still valid. For this purpose, the portable gas measuring device performs a validity test 39 for the calibration, in which it is checked whether the present calibration data 32 are, for example, not more than twelve hours old. If the calibration is no longer valid, a new calibration measurement 31 has to be performed before the next measurement 41. Before the new calibration measurement, the portable gas measuring device executes a function test, in which a further algorithm concludes adequate functionality from the preceding series of measurements and the preceding calibration measurement. If the portable gas measuring device does not pass this function test 29, the portable gas measuring device recommends or requires a repair 19, after which a new factory calibration for replaced components by the producer will possibly become necessary. It is to be emphasized that in the described variant of the method, only the calibration measurement on the gas standard, the program selection, and the execution of measurements are actively executed by the user, while the analysis 50 and the self-test 39, 29 can each be computed automatically and in a fraction of a second from the databases 12, 22, 32, 42, 52.

Exemplary Embodiment 2

Figure 4:
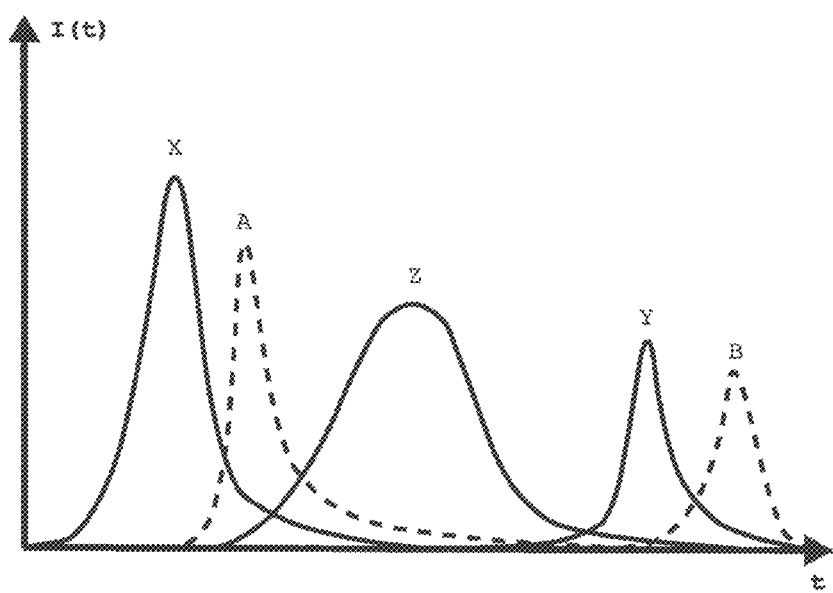
FIG. 4 shows a schematic gas chromatogram of a multidimensional standard and a corresponding sample.
Figure 2:
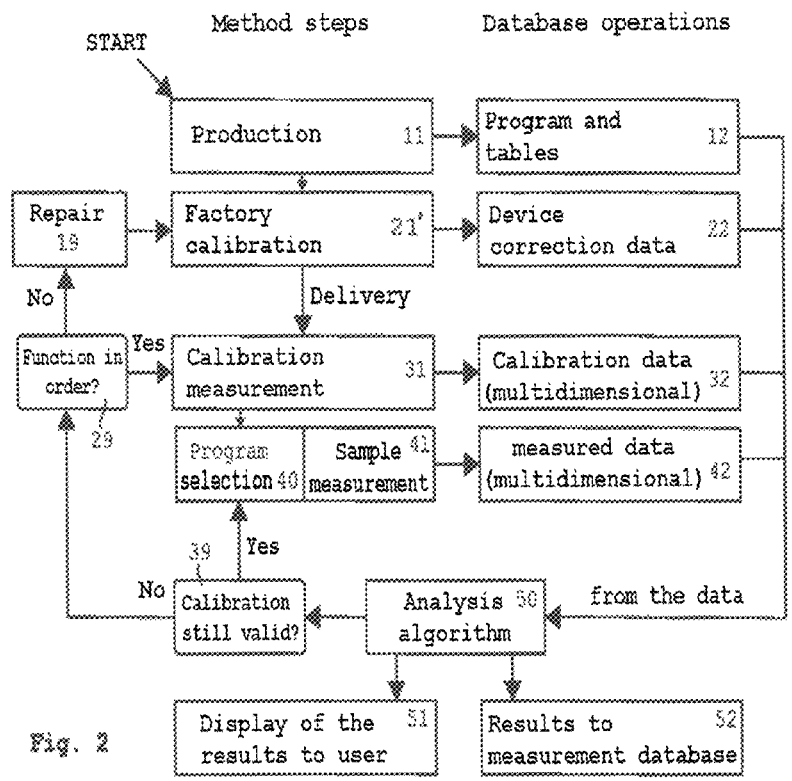
FIG. 2 shows a method sequence according to a first exemplary embodiment.
Figure 3:
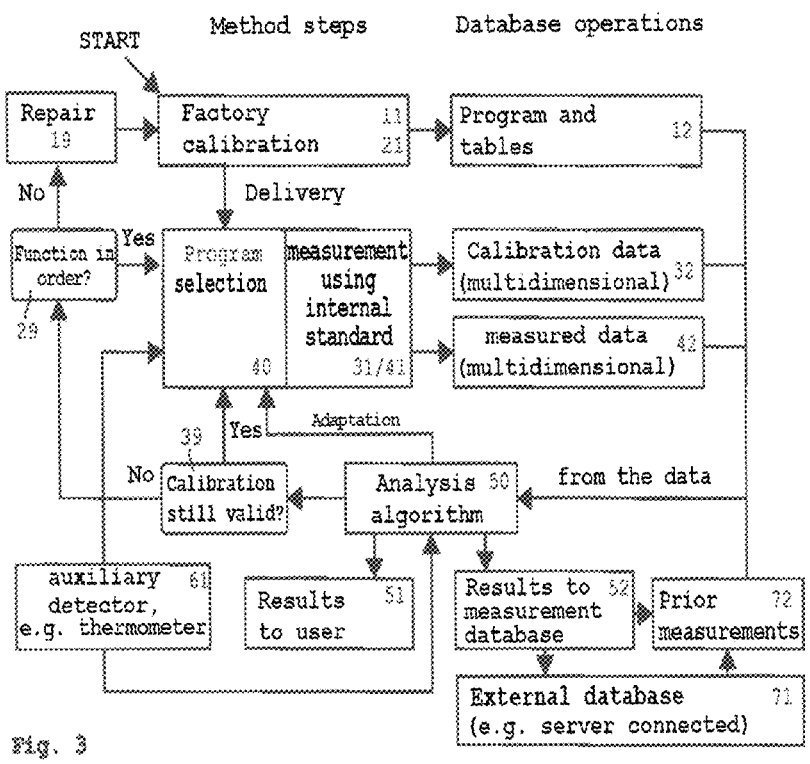
FIG. 3 shows a method sequence according to a second exemplary embodiment.

In a second exemplary embodiment, the gas measuring device is a portable gas chromatograph for measuring volatile organic compounds. The producer tests the function of the portable gas measuring device after the production 11 and stores correction values 21, which are determined during an array of calibration measurements on different samples, in a database in the gas measuring device. The correction values by the producer are factors determined as average values, wherein these are, for example, performance coefficients of the fan and the retention and response coefficients for each individual material measured by the producer during the calibration. Coefficients for further materials are extrapolated. A database having various materials and the characteristic peaks in the chromatograms thereof is also installed 12 on the gas measuring device by the producer, which also contain an experimentally determined factor, which converts the signal level of the detector unit used into a material concentration. In the calibration by the user on a gas standard 9, a chromatogram for this gas standard 9 in the environmental conditions of the measurement is stored 32. This reference measurement is used to calibrate the chromatogram of the measurement with respect to both dimensions. Before the measurement, a program is selected 40 in this case, which determines, on the one hand, the parameters of the measurement and, on the other hand, the model and the starting values of the analysis. The user only has to select one program in each case, firstly the program for calibration and then the program of the target material, and trigger 41 the measurements. Calibration and analysis including all corrections are performed automatically, wherein the composition and concentration of the materials are displayed as a result. The calibration measurement does not have to be part of each measurement in this case, because the stock of the gas standard can be saved by omitting the calibration and accordingly costs and weight for carrying along the gas standard in the field test can be saved. As schematically shown in FIG. 4, the calibration data 32 and measured data 42 are superimposed in a common multidimensional measurement curve. With the exception of problem cases and special cases, it is possible for a well-programmed algorithm on the basis of the position of signal peaks to assign the components of the signal and to separate the combined measurement into its components. During the analysis 50, additional data are used in this second exemplary embodiment, namely a database having prior measurements 72, which were performed using the same measuring program 40, and a measured value of an auxiliary detector on the gas measuring device, for example, a thermometer, which records the external temperature. This database is advantageously supplemented with additional measured data from an external database 71. Further advantageous auxiliary data are, for example, the serial number of the gas measuring device, the point in time of the measurement, and the GPS coordinates of the measurement, items of information which permit multiple measurements to be linked. From the available data, the automatic analysis mechanism can take into consideration internal and external changes for the special gas measuring device at a specific location and its deviation from the production series in the algorithms and even compute advantageous adaptations to the program selection, which are proposed to the user or even implemented automatically. The factory calibration is replaced by the iterative adaptation of the program (in comparison to the first exemplary embodiment), since the gas measuring device finds its optimum parameters itself. Gradual worsening of components can also be compensated in a limited scope by the program, to pass the self-tests 39, 29 longer (i.e., to also actually function in the limits specified therein), whereby additional calibrations and/or repairs are avoided. In this variant, only one program is actively selected by the user, the fine settings of which can be iteratively adapted by the automatic mechanism, and the measurement is executed on the sample without great preparation. Therefore, a previously unreached level of comfort and a high speed in execution of measurements exist for the user. In contrast, there are higher demands on the automatic mechanisms and the tolerances in the production.

To illustrate the definition of a multidimensional measured variable, an exemplary measurement signal of a measurement of the signal $I(t)$ is shown in FIG. 4, wherein $I$ is the signal strength and $t$ is the second dimension of the measurement. It is to be noted in this case that $t$ is not the point in time of the measurement, i.e., $I(T)$ as in a one-dimensional measurement, but rather $I(t, T)$ applies. In gas chromatography, the measurement signals typically have the form of multiple, possibly superimposed peaks having possibly asymmetrical flanks, which are recorded as signals of target materials $(X, Y, Z)$ and reference materials $(A, B)$ in one or successive measurements. In a gas chromatograph having photoionization detector, $I$ is the signal at the detector unit and $t$ is the retention time in the gas chromatograph. Typically firstly a device function is applied to the raw data of the measurement, before it is displayed in a comprehensible form and can be analyzed. The methodology and mathematical implementation of the analysis algorithms in all cases mentioned is conventionally a manual assignment of the peaks to experiential values or advantageously an automated simulation of peaks (for example, as a modified Gaussian distribution or related functions), which are applied via an iterative method to the measurement curve and furthermore can advantageously be automatically assigned to the experiential or theoretical values of target materials. The illustrated signal in FIG. 4 is a simple case having clearly defined and separable peaks, in which a manual, possibly computer-assisted analysis is possible without problems. Simple fully automatic analysis algorithms without corrections would also have no problem with this example. In contrast, if overlaps occur, the measurement is strongly disturbed by background signals and noise, or if some peaks are located just at the limit of what is measurable, a complex and standardized method for calibrating, measuring, and analyzing becomes necessary to enable a reliable assignment of the signal components. So-called cross sensitivities represent a special challenge, in which two target materials have very similar signal characteristics, which overlap, or the measurement is even not independent, because the target materials mutually influence one another in the measuring process and/or the gas measuring device.

Figure 5A:
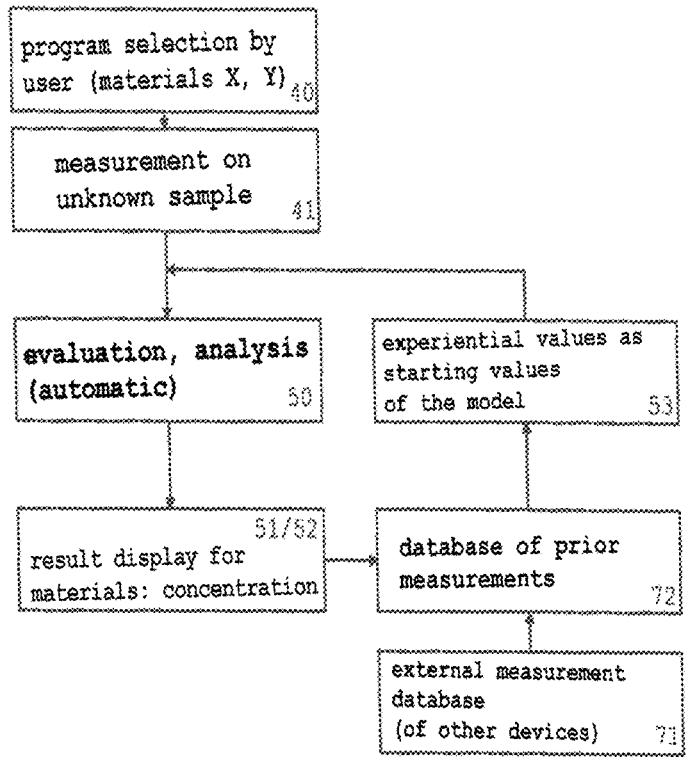
FIGS. 5a and 5b show method sequences for iterative adaptation.
Figure 5B:
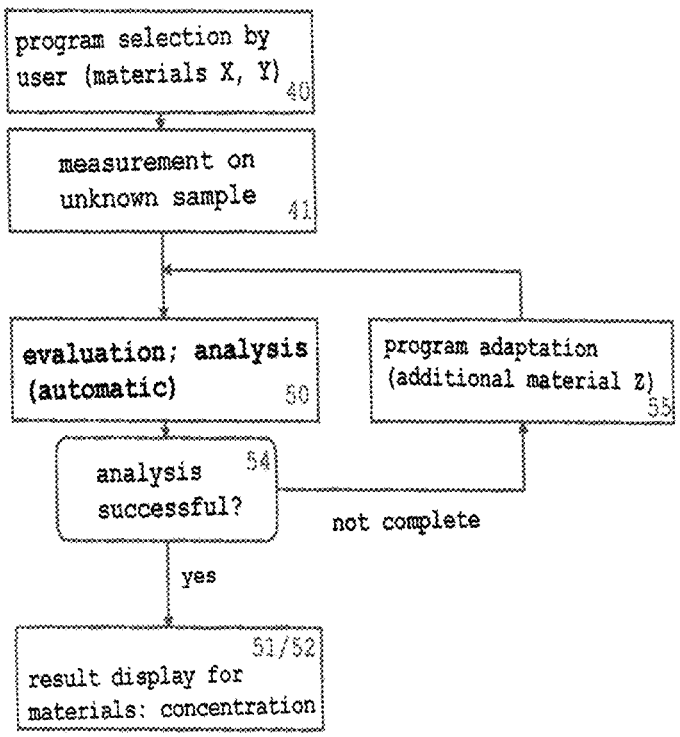

Two details of the method, using which the quality of the analysis can be improved, are shown in FIG. 5. In the method illustrated in FIG. 5a, a measuring program is selected for two target materials (X, Y) and the measurement is performed on an unknown sample. The automated analysis program determines as a result the concentration values for these materials and stores the measurements (not only the results, but rather also further intermediate values or even the raw data) in a database, which are compiled by an external database with the measurements which were carried out using the same program on other gas measuring devices. Experiential values 53 can now be computed from these data, which may be used in particular as starting values of the model for a simulation during further measurements. Limits of the simulation or the adaptation of such parameters to the model, which are not varied in the simulation, can thus also be iteratively improved. In this manner, the model is improved, and the gas measuring device learns automatically. Errors can also be caught and repetitions of the measurement can be avoided by automatic adaptations to the model. In the method illustrated in FIG. 5b, after the measurement on an unknown sample using a program for two target materials (X, Y), it is tested whether the analysis was successful 54 (for example, whether the simulated peaks for X and Y are superimposed with the entire signal with limited difference) or whether signal parts cannot be assigned. If the analysis is evaluated as "not successful", in a program loop 55, the analysis is repeatedly called using additional target materials until a further target material (Z) (and/or another program) is found, which meets the condition for a successful analysis (or another exit condition ends the loop).

Figure 6A:
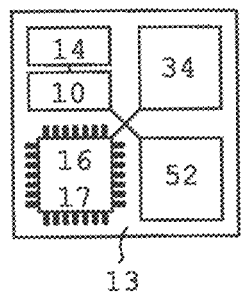
FIG. 6a shows a gas measuring device according to a further exemplary embodiment, having integrated detector unit, operating and display unit, and control and analysis unit having database.
Figure 6B:
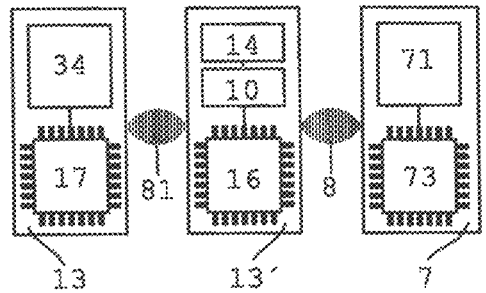
FIG. 6b shows a variant having a group of gas measuring devices, which are coupled via network connections.
Figure 6C:
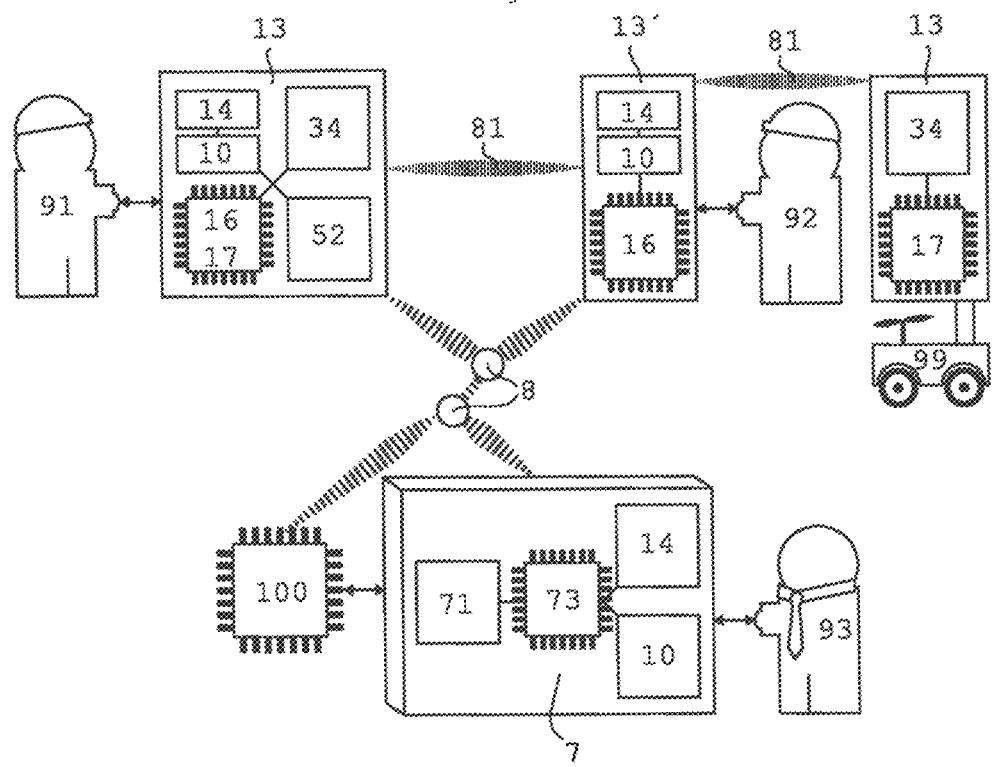
FIG. 6c shows a group of multiple gas measuring devices and users.

FIG. 6 shows multiple variants of how the various physical components of the measuring device are connected. As shown in FIG. 6a, the gas measuring device 1 can be embodied as an integrated gas measuring device having detector unit 34, control and analysis unit 16/17, and internal database 52 and can have a separate operating unit 10 and display unit 14. In another variant (implemented by the applicant), the gas measuring device is embodied in two parts, as a gas measuring device 1' having detector unit 34 and control unit 17 and a second detached device 13', which are connected together wirelessly via Bluetooth, wherein the detached device 13' is specifically a smart phone having touchscreen 10, 14 and the smart phone is furthermore connected via WLAN and/or a mobile Internet connection to an external processing unit, a server 7, which has a separate processing unit 73 and an external database 71. In a third variant, the two prior variants are in a functional group of multiple gas measuring devices and multiple users 91, 92, 93, wherein the server is embodied as a control center having separate operating and display elements 10, 14 and additionally a higher-performance computer 100 assumes a part of the control of the operation. In one advantageous embodiment, also as shown in FIG. 6c, a gas measuring device, which is controlled by a user 92 using the detached device 13', is placed on a carrier unit 99, in the example a driving and flight-capable drone, which is advantageously embodied as self-controlled. This drone-carried gas measuring device can reach locations which are difficult to access and can be used in particularly hazardous situations, in particular the search for highly toxic and/or explosive target materials.

The invention claimed is:

1. A method for a multistep calibration of a portable gas measuring device having a detector unit for gas chromatography for selective detection of a plurality of chemical compounds that is connected to a control unit and an analysis unit, the method comprising:
performing a two-part calibration comprising:
in a first part of the two-part calibration that is performed in a factory, performing a factory setting of at least one of the portable gas measuring device and a device associated with the portable gas measuring device and generating a database that comprises values for a plurality of target materials and/or values for a plurality of measuring programs for the portable gas measuring device, and
in a second part of the two-part calibration that is performed by at least one user in the field, connecting at least one container having a known gas standard to the portable gas measuring device by the at least one user and performing a reference measurement on the known gas standard, wherein a multidimensional reference measurement is recorded,
selecting, by the at least one user in the field, a measuring program for one or more target materials from a list of measuring programs that were installed on the device by a producer or prepared by the at least one user, the measuring program being a controlled sequence of measuring,
performing a measurement by the portable gas measuring device on a sample, wherein the control unit executes the measuring program in dependence on the selected measuring program, wherein a multidimensional measured variable is recorded,
automatically performing an analysis by the analysis unit to identify at least one of the one or more target materials that is present in the sample and the respective concentrations thereof, wherein the analysis is based on:
the factory calibration for the portable gas measuring device and the values for the plurality of target materials and/or the values for the plurality of measuring programs from the first part of the two-part calibration,
the multidimensional reference measurement for the gas standard from the second part of the two-part calibration, and
the multidimensional measured variable from the measurement on the sample, and
repeating the second part of the two-part calibration by the at least one user in the field prior to performing at least one subsequent sample measurement by connecting the at least one container having the known gas standard to the portable gas measuring device by the at least one user and repeating the reference measurement on the known gas standard.

2. The method of claim 1, wherein performing the factory setting comprises determining separate device correction values for the portable gas measuring device and stored in a database.

3. The method of claim 1, wherein the gas measuring device is a gas chromatograph that is a portable measuring device for field tests of less than 1.5 kg total weight.

4. The method of claim 1, wherein the gas standard is a gas mixture having one or more harmless materials that are not harmful to health or are present in harmless concentrations, as defined by a workplace safety standard, and at least one of the one or more target materials in the sample is a health-hazardous material in a hazardous concentration in the sample, as defined by the workplace safety standard.

5. The method of claim 1, wherein a gas mixture of the materials isobutene in harmless concentration, as defined by a workplace safety standard, and toluene in harmless concentration, as defined by the workplace safety standard, is used as the gas standard for the reference measurement, wherein the one or more target materials of the selected measuring program of the sample measurement are benzene and 1,3-butadiene, wherein a detection limit of the portable gas measuring device of at least one of the benzene and 1,3-butadiene is less than 1 ppm, and wherein signal components of further unknown materials in the measurement signal can also be differentiated from signal components of the target materials in the analysis.

6. The method of claim 5, wherein the concentration of at least one of the isobutene and the toluene is between 1 ppm and 100 ppm in air or nitrogen.

7. The method of claim 1, wherein the portable gas measuring device is equipped with or connected to a mobile processing unit, which can access databases of external processing units via a wireless connection.

8. The method of claim 7, wherein additional data processed during the analysis are retrieved from external databases by the portable gas measuring device.

9. The method of claim 1, wherein the portable gas measuring device stores multidimensional measured variables of successive measurements in a database and carries out a function test of the portable measuring device from the reference measurement, and one or more items of information are displayed to the at least one user about the state of the portable gas measuring device based on the function test.

10. The method of claim 9, wherein the one or more items of information comprises a warning about required maintenance.

11. The method of claim 1, wherein the portable gas measuring device incorporates prior measurement results, which were also generated using the selected program, from an internal database in the analysis.

12. The method of claim 1, wherein the portable gas measuring device incorporates measurement results, which were also generated using the selected program by other portable gas measuring devices of the same type, from an internal or external database in the analysis.

13. The method of claim 1, wherein the measuring program is automatically adapted to measurement results of one or more auxiliary detectors.

14. The method of claim 13, wherein the measurement results of one or more auxiliary detectors comprises an external temperature.

15. The method of claim 1, wherein the portable gas measuring device automatically proposes changes to the measuring program to the at least one user that have been computed in an algorithm from prior measurements stored in databases as parameters.

16. The method of claim 1, wherein during the analysis, after a preceding pass of the analysis has been evaluated as failed according to specific criteria, subsequently further target materials are added from a database into the analysis, which supplement the measuring program selected by the at least one user, wherein the addition of further target materials to the analysis is repeated until either:
the analysis becomes successful, or
at least one of: a specific number of repetitions is exceeded and a time span is exceeded.

17. The method of claim 1, wherein a measuring program for multiple target materials is selected and a control program for the measurement, an algorithm of the analysis, or both is automatically adapted so that a known cross sensitivity for the multiple target materials is avoided.

18. The method of claim 1, wherein the measurement on the sample is carried out in parallel by multiple users, and the selection of the measuring program, data, or both are transferred between multiple portable gas measuring devices-connected in a network, to a central server or both.

19. The method of claim 1, wherein the portable gas measuring device is used as a part or an attachment on at least one of a vehicle and an aircraft and the gas measuring device is connected via a wireless connection to an external processing unit.

20. The method of claim 19, wherein the at least one of a vehicle and an aircraft is a robot drone that is remote-controlled by the at least one user or self-controlled.

21. The method of claim 1, wherein the multidimensional reference measurement is a gas chromatogram.

22. A method for a multistep calibration of a portable gas measuring device having a detector unit for gas chromatography for selective detection of a plurality of chemical compounds that is connected to a control unit and an analysis unit, the method comprising:
in a first part of a two-part calibration, performing a factory setting of at least one of the portable gas measuring device and a device associated with the portable gas measuring device and generating a database that comprises values for a plurality of target materials and/or values for a plurality of measuring programs for the portable gas measuring device,
selecting, by at least one user in the field, a measuring program for one or more target materials from a list of measuring programs that were installed on the device by a producer or prepared by the at least one user, the measuring program being a controlled sequence of measuring,
performing a measurement by the portable gas measuring device on a sample, wherein the control unit executes the measuring program in dependence on the selected measuring program, wherein a multidimensional measured variable is recorded in which a signal of the sample is superimposed with a signal generated by performing a reference measurement that is based on a known gas standard that is mixed with the sample in the portable gas measuring device by the at least one user in the field in a second part of the two-part calibration,
automatically performing an analysis by the analysis unit to identify at least one of the one or more target materials that is present in the sample and the respective concentrations thereof, wherein the analysis is based on separating the signal of the sample and the signal of the reference out of the multidimensional measured variable and processing the signal of the sample and the signal of the reference together with values of the one or more target materials and the factory setting of the at least one of the portable gas measuring device and the device associated with the portable gas measuring device, and repeating the second part of the two-part calibration by the at least one user in the field prior to performing at least one subsequent sample measurement by repeating the reference measurement that is based on the known gas standard.

23. The method of claim 22, wherein the multidimensional measured variable is a gas chromatogram.

* * * * *